(12) United States Patent
Peters et al.

(10) Patent No.: US 6,617,459 B2
(45) Date of Patent: Sep. 9, 2003

(54) AZABICYCLO DERIVATIVES AND THEIR USE

(75) Inventors: Dan Peters, Sverige (SE); Jørgen Scheel-Krüger, Glostrup (DK); Elsebet Østergaard Nielsen, København (DK)

(73) Assignee: NeuroSearch A/S, Ballerup (DK)

( * ) Notice: Subject to any disclaimer, the term of this patent is extended or adjusted under 35 U.S.C. 154(b) by 0 days.

(21) Appl. No.: 09/855,630

(22) Filed: May 15, 2001

(65) Prior Publication Data

US 2001/0047028 A1 Nov. 29, 2001

Related U.S. Application Data

(63) Continuation of application No. PCT/DK00/00038, filed on Jan. 28, 2000.

(30) Foreign Application Priority Data

Jan. 28, 1999 (DK) ......................................... 1999 00106
Jul. 1, 1999 (DK) ......................................... 1999 00950

(51) Int. Cl.[7] ........................ C07D 451/04; A61K 51/00
(52) U.S. Cl. ...................... 548/124; 548/125; 424/1.81; 424/1.85; 424/1.89
(58) Field of Search ............................. 424/1.81, 1.85, 424/1.89; 548/124, 125; 514/304

(56) References Cited

U.S. PATENT DOCUMENTS 3,509,161 A    4/1970   Dold et al.

FOREIGN PATENT DOCUMENTS

| WO | 9631508 | 10/1996 |
|---|---|---|
| WO | 9713770 | 4/1997 |
| WO | 9846600 | 10/1998 |
| WO | 9854181 | 12/1998 |
| WO | 9854182 | 12/1998 |
| WO | 9938866 | 8/1999 |

OTHER PUBLICATIONS

Pierre Blier and Claude de Montigny, vol. 15, 1994, Elsevier Science Ltd pp 220–226.

Paul Willner, Department of psychology, (1990) pp 141–156.

Christopher J. Bench et al., From the academic Department of psychiatry, Psychological Medicine, 1992 pp 607–615.

R J Dolan, C J Bench, R G Brown et al., Journal of Neurology, Neurosurgery, and psychiatry (1992) pp768–773.

*Primary Examiner*—Michael G. Hartley
(74) *Attorney, Agent, or Firm*—Birch, Stewart, Kolasch & Birch, LLP

(57) ABSTRACT

The present invention relates to 8-azabicyclo[3.2.1]oct-2-ene derivatives in their labelled form. Furthermore, the present invention relates to the use of said derivatives in their labelled or unlabelled form in diagnostic methods, in particular for in vivo receptor imaging (neuroimaging).

5 Claims, No Drawings

AZABICYCLO DERIVATIVES AND THEIR USE

This application is a continuation of PCT/DK00/00038, filed Jan. 28, 2000.

TECHNICAL FIELD

The present invention relates to azabicyclo derivatives in their labelled and unlabelled form. Furthermore, the present invention relates to the use of said derivatives in their labelled or unlabelled form in diagnostic methods, in particular for in vivo receptor imaging (neuroimaging).

BACKGROUND ART

WO 9713770 discloses 8-azabicyclo[3.2.1]oct-2-ene derivatives which are re-uptake inhibitors for the monoamine neurotransmitter serotonine (5-hydroxy-tryptamine, 5-HT) and therefore useful in the treatment of disorders or diseases which are caused, at least in part, by increase or decrease of the endogenous serotonine levels. Such disorders or diseases are e.g., depression and related disorders, obsessive compulsive disorders, panic disorders, memory deficits, attention deficit, hyperactivity disorder, obesity, anxiety and eating disorders.

Monoamine neurotransmitters (i.e. serotonine, dopamine, and noradrenaline) are produced in neurons and are released into the synaptic cleft upon stimulation of the presynaptic neuron. The neurotransmitter molecules can diffuse through the cleft and then bind to specific receptor molecules (transporters) located in the postsynaptic cell membrane. Binding to these receptors results in polarisation of the cell, i.e. transduction of the stimulus. The removal (or inactivation) of monoamine neurotransmitters from the synaptic cleft occurs mainly by a re-uptake mechanism into presynaptic nerve terminals. By inhibiting the re-uptake an enhancement of the physiological activity of monoamine neurotransmitters occurs.

Major depression is a common disorder, affecting approximately 1 in 6 individuals at some point in their lives. The pathophysiology of depression is poorly understood so far, and several neurotransmitters have been implicated in the pathophysiology of major depression. Inhibitors that block noradrenaline and serotonine re-uptake are currently used as pharmaceuticals in anti-depressant therapy. Several lines of preclinical and clinical evidence indicate that an enhancement of serotonine-mediated neurotransmission might underlie the therapeutic effect of the most recent and currently used drugs in anti-depressant therapy, such as fluoxetine, citalopram and paroxetine [P. Blier & C de Montigney; *TIPS* (Review) 1994 15 220–225].

Paradoxically, serotonine re-uptake inhibitors block the serotonine transporter within minutes after application whereas their full anti-depressant effect is seen only after three to four weeks of treatment, indicating that re-uptake inhibition per se is not responsible for the anti-depressant response, but rather that further adaptive changes underlie and/or contribute to their therapeutic effect [P. Willner; *Int. Review of Psychiatry* 1990 2 141–156].

The serotonergic neural system of the brain has been shown to influence a variety of physiologic functions, and disturbance of this system has been made responsible for a variety of diseases and disorders such as eating disorders, depression, obsessive compulsive disorders, panic disorders, alcoholism, pain, memory deficits and anxiety. Included among these disorders are depression and related disorders such as pseudodementia or Ganser's syndrome, migraine, pain, bulimia, obesity, pre-menstrual syndrome or late luteal phase syndrome, alcoholism, tobacco abuse, panic disorder, anxiety, post-traumatic syndrome, memory loss, dementia of ageing, social phobia, attention deficit hyperactivity disorder (ADHD syndrome), chronic fatigue syndrome, premature ejaculation, erectile dysfunction, anorexia nervosa, disorders of sleep, autism, mutism or trichotillomania.

Currently the standard method for the diagnosis of depression is a consultation between physician e.g., psychiatrists and patient in order to evaluate the patient's emotional life. It is characteristic for depressed patients e.g. to lack initiative and interest, to possess a general feeling of sadness, and to have a feeling of guilt and worthlessness, to lack appetite and libido, and to suffer from sleeplessness. These symptoms can occur temporarily and with different intensity which makes it very difficult to determine the appropriate diagnosis and therapy. Therefore, psychiatrists have looked for objective laboratory or clinical tests that could confirm the diagnosis and possibly predict a response to treatment.

Recent research has focused on the biochemical backgrounds of the depression syndrome. It has been found that measurements of the regional cerebral blood-flow (rCBF) can be used to diagnose depression. In brains of depressed patients three areas showed significantly reduced rCBF (left dorsolateral prefrontal cortex, the left anterior cingulate cortex and the left angular gyrus). When depression is combined with cognitive impairment a decreased rCBF in the left medial prefrontal cortex and increased rCSF in the right cerebral vermis has been detected [Bench C J, Friston K J, Brown R G, Scott L C, Frackowiak R S & Dolan R J: The anatomy of melancholia-focal abnormalities of cerebral blood flow in major depression; *Psychol-Med.* 1992 22 (3) 607–15; and Dolan R J, Bench C J, Brown R G, Scott L C, Friston K J & Frackowiak-R S: Regional cerebral blood flow abnormalities in depressed patients with cognitive impairment; *J. Neurol. Neurosurg. Psychiatry.* 1992 56 (9) 768–73]. This method enables a physician to reliably detect a parameter that seems to correlate at least in a number of cases with pathologic depression. However, treatment with anti-depressant drugs is not reflected in changes of the rCBF, which means that a therapeutic effect can not be monitored by this method.

The study of serotonine re-uptake sites using emission tomography requires the use of radioligands which have desirable properties for in vivo receptor imaging. These criteria include ease of labelling with positron-emitting radio-nucleotides, low rates of peripheral metabolism, high selectivity for brain regions holding the neuroreceptor of interest, and relatively high specific/non-specific binding ratios. Despite the development of a number of radioligands for the serotonine transporter, none of these compounds satisfactorily meet all the criteria desired for an ideal ligand.

SUMMARY OF THE INVENTION

The novel compounds and their derivatives of this invention are very specific and selective binders to serotonine transporters. This allows to reliably determine the number of serotonine binding sites and related Kd values and the release of serotonine as well as the detection of changes in the serotonine metabolism in response to therapeutic drugs.

It is therefore an object of the present invention to provide a compound which can be used in the treatment or diagnosis of diseases or disorders that are related to changes in the serotonine levels in vivo and in vitro and which can be used as well to monitor the effect of a therapy.

Further, it is an object of the present invention to provide methods for diagnosing several disorders linked to decreased or increased neurotransmission of serotonine in vivo and in vitro using a specific detectable compound.

DETAILED DISCLOSURE OF THE INVENTION

It is an object of the present invention to provide a compound which can be used for treatment and/or diagnosing diseases or disorders that are related to changes in the serotonine levels in vivo and in vitro and which can be used as well to monitor the effect of a therapy. This object is solved by providing a labelled or unlabelled compounds derived from a compound having the formula (I):

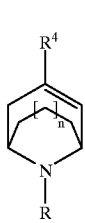

(I)

or any of its enantiomers or any mixture thereof, or a pharmaceutically acceptable salt thereof; wherein n is 0 or 1;

R is hydrogen, alkyl, haloalkyl, alkenyl, haloalkenyl, alkynyl, haloalkynyl, cycloalkyl, cycloalkylalkyl or 2-hydroxyethyl, alkylthio, alkylamino or a leaving group and $R^4$ is phenyl which may be substituted one or more times with substituents selected from the group consisting of halogen, $CF_3$, $OCF_3$, CN, amino, alkylamino, nitro, alkyl, haloalkyl, hydroxyalkyl, cycloalkyl, alkenyl, haloalkenyl, alkynyl, haloalkynyl, amino, nitro, heteroaryl, aryl, —O—R", wherein (R") represents alkyl, alkenyl, alkynyl, cycloalkyl, haloalkyl, hydroxyalkyl, aminoalkyl, haloalkenyl, haloalkynyl;

3,4-methylenedioxyphenyl;

benzyl which may be substituted one or more times with substituents selected from the group consisting of halogen, $CF_3$, $OCF_3$, CN, amino, alkylamino, nitro, alkyl, haloalkyl, hydroxyalkyl, cycloalkyl, alkenyl, haloalkenyl, alkynyl, haloalkenyl, amino, nitro, heteroaryl, aryl, —O—R", wherein (R") represents alkyl, alkenyl, alkynyl, cycloalkyl, haloalkyl, hydroxyalkyl, aminoalkyl, haloalkenyl, haloalkynyl;

heteroaryl which may be substituted one or more times with substituents selected from the group consisting of halogen, $CF_3$, $OCF_3$, CN, amino, alkylamino, nitro, alkyl, haloalkyl, hydroxyalkyl, cycloalkyl, alkenyl, haloalkenyl, alkynyl, haloalkenyl, amino, nitro, heteroaryl, aryl, —O—R", wherein (R") represents alkyl, alkenyl, alkynyl, cycloalkyl, haloalkyl, hydroxyalkyl, aminoalkyl, haloalkenyl, haloalkynyl;

naphthyl which may be substituted one or more times with substituents selected from the group consisting of halogen, $CF_3$, $OCF_3$, CN, amino, alkylamino, nitro, alkyl, haloalkyl, hydroxyalkyl, cycloalkyl, alkenyl, haloalkenyl, alkynyl, haloalkenyl, amino, nitro, heteroaryl, aryl, —O—R", wherein (R") represents alkyl, alkenyl, alkynyl, cycloalkyl, haloalkyl, hydroxyalkyl, aminoalkyl, haloalkenyl, haloalkynyl;

a fluorescent group.

or a compound of formula (I) containing a radioactive label.

In the compound of formula (I) R is preferably hydrogen, an alkyl group having 1 to 6 C atoms, haloalkyl, haloalkenyl and $R^4$ is preferably a phenyl group which may be substituted one or more times. The substituents are preferably selected from I, F, $CF_3$, $OCF_3$, CN, $NO_2$, $CH_3$, $OCH_3$, or —O—R" wherein R" represents alkyl, alkenyl, alkynyl, haloalkyl, haloalkenyl, haloalkynyl, hydroxyalkyl, aminoalkyl;

Especially preferred compounds of formula(I) are (±)-3-(4-trifluoromethoxyphenyl)-8-methyl-azabicyclo [3.2.1]oct-2-ene;

(±)-3-(4-trifluoromethoxyphenyl)-8-azabicyclo[3.2.1]oct-2-ene;

(±)-3-(4-cyanophenyl)-8-azabicyclo[3.2.1]oct-2-ene;

(±)-3-(4-cyanophenyl)-8-methyl-azabicyclo[3.2.1]oct-2-ene;

(±)-3-(4-nitrophenyl)-8-methyl-azabicyclo[3.2.1]oct-2-ene;

(±)-3-(4-nitrophenyl)-8-azabicyclo[3.2.1]oct-2-ene;

(±)-3-(4-(4,4,4,3,3,2,2,1,1-nona-fluoro-butyl-1-oxy) phenyl)-8-azabicyclo[3.2.1]oct-2-ene;

(±)-3-(4-(4,4,4,3,3,2,2,1,1-nona-fluoro-butyl-1-oxy) phenyl)-8-methyl-8-azabicyclo[3.2.1]oct-2-ene;

(±)-3-(4-(2,2,2-trifluoroethyl-1-oxy)phenyl)-8-azabicyclo [3.2.1]oct-2-ene;

(±)-3-(4-(2,2,2-trifluoroethyl-1-oxy)phenyl)-8-azabicyclo [3.2.1]oct-2-ene;

(±)-3-(4-(ethylen-1-oxy)phenyl)-8-azabicyclo[3.2.1]oct-2-ene;

(±)-3-(4-(ethylen-1-oxy)phenyl)-8-methyl-8-azabicyclo [3.2.1]oct-2-ene;

(±)-3-(4-(2-propylen-1-oxy)phenyl)-8-azabicyclo[3.2.1]oct-2-ene; or (±)-3-(4-(2-propylen-1-oxy)phenyl)-8-methyl-8-azabicyclo [3.2.1]oct-2-ene.

(±)3-[1-(4-trifluoromethoxyphenyl)]-9-azabicyclo[3.3.1] non-2-ene;

(±)3-[1-(4-trifluoromethylphenyl)]-9-azabicyclo[3.3.1]non-2-ene;

(±)-9-Methyl-3-[1-(4-trifluoromethoxyphenyl)]-9-azabicyclo[3.3.1]non-2-ene;

(±)-9-Methyl-3-[1-(4-trifluoromethylphenyl)]-9-azabicyclo [3.3.1]non-2-ene;

or a pharmaceutical acceptable addition salt thereof as well as the same compounds which are labelled with at least one nuclide selected from $^{11}C$, $^{18}F$ and $^{13}N$, or a pharmaceutically acceptable salt of said labelled compound.

Other preferred compounds of formula (I) are compounds wherein R represents a haloalkenyl such as 1-iodo-prop-1-en-3-yl, wherein the iodine is a radioactive isotope of iodine and $R^4$ represents phenyl substituted with —$C_4F_9$, —$CH_2CF_3$, —CH═$CH_2$, $CH_2$CH═$CH_2$, F, CN, $CH_3$, $CF_3$, $OCF_3$, Cl, H, $NO_2$; or $R^4$ represents 3,4-dichlorophenyl.

Further preferred compounds are compounds of formula (I) wherein R represents a haloalkyl such as methyliodine, ethyliodine, propyliodine, methylflouride, ethylfluoride, propylfluoride wherein the halogen is a radioactive isotope of iodine or fluoride and $R^4$ represents phenyl substituted —$C_4F_9$, —$CH_2CF_3$, —CH═$CH_2$, $CH_2$CH═$CH_2$, F, CN, $CH_3$, $CF_3$, $OCF_3$, Cl, H, $NO_2$; or $R^4$ represents 3,4-dichlorophenyl.

Other preferred compounds are compounds of formula(I) wherein R represents a alkylthio-derivative such as thiomethyl, ethylthio, propylthio, butylthio and $R^4$ represents phenyl substituted with —$C_4F_9$, —$CH_2CF_3$, —CH═$CH_2$, $CH_2$CH═$CH_2$, F, CN, $CH_3$, $CF_3$, $OCF_3$, Cl, H, $NO_2$; or $R^4$ represents 3,4-dichlorophenyl. These compounds are suitable for co-ordinating to a $^{99m}Tc$ complex.

Definition of Substituents

In the context of this invention halogen represents a fluorine, a chlorine, a bromine or a iodine atom.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In a preferred embodiment of this invention alkyl represents a $C_{1-3}$-alkyl group, which may in particular be methyl, ethyl, propyl or isopropyl.

In the context of this invention a haloalkyl group designates an alkyl as above, mono- or polysubstituted with halogen as above. This includes e.g. (X designates a halogen as above) $CX_3$, $CHX_2$, $CH_2X$, $CH_2CX_3$, $CH_2CH_2X$, $XCHCH_2X$, $C_3H_6X$, $C_3H_5X_2$, $C_3H_4X_3$, $C_3H_3X_4$, $C_3H_2X_5$, $C_3X_7$ etc. Preferred groups are $C_{1-4}$-haloalkyl; Especially preferred groups are —$CH_2F$, $CH_2I$, —$C_2H_5I$, —$C_2H_5F$, $C_3H_6I$, $C_3H_6F$, —$CF_3$, —$CH_2CF_3$, —$C_4F_9$.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, and cyclohexyl.

In the context of this invention an alkenyl group designates a carbon chain containing one or more double bonds, including di-enes, tri-enes and poly-enes. In a preferred embodiment the alkenyl group of the invention comprises of from two to six carbon atoms ($C_{2-6}$-alkenyl), including at least one double bond. In a most preferred embodiment the alkenyl group of the invention is ethenyl; 1- or 2-propenyl; or 1-, 2-, or 3-butenyl.

In the context of this invention a haloalkenyl group designates a alkenyl group as above mono- or polysubstituted with halogen as above. In a preferred embodiment of the invention the haloalkenyl represents from 2 to 4 carbons monosubstituted with halogen such as —$CH_2CH=CHI$, —$CH_2CH=CHF$, —$CH=CHF$, —$CH=CHI$, —$CF=CH_2$, $CH=CF_2$, —$CH=CHCH_2I$, —$CH=CHCH_2F$, —$CH=CH—CH=CHI$, —$CH=CH—CH=CHF$, —$CH_2CH_2CH=CHI$, —$CH_2CH_2CH=CHI$, etc.

In the context of this invention an alkynyl group designates a carbon chain containing one or more triple bonds, including di-ynes, tri-ynes and poly-ynes. In a preferred embodiment the alkynyl group of the invention comprises of from two to six carbon atoms ($C_{2-6}$-alkynyl), including at least one triple bond. In its most preferred embodiment the alkynyl group of the invention is ethynyl, 1,2- or 2,3-propynyl, 1,2-, 2,3- or 3,4-butynyl.

In the context of this invention a haloalkynyl group designates a alkynyl as described above, mono or poly substituted with a halogen as above. In a preferred embodiment of the invention, the haloalkynyl is an alkynyl having 2–4 carbons containing one triple bond and one halogen atom. Examples are e.g. —C C—$CH_2I$, —C C—$CH_2F$, —C C—$CH_2Cl$, —CHI—C CH, —CHF—C CH, —CHCl—C CH, —$CH_2C$ C—$CH_2I$, —$CH_2C$ C—$CH_2Cl$, —$CH_2C$ C—$CH_2F$, etc.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above.

In the context of this invention an haloalkoxy group represents an alkoxy group as above substituted with one or more halogens as above.

In the context of this invention an alkoxy-alkyl group designates an "alkyl-O-alkyl—" group, wherein alkyl is as defined above.

In the context of this invention an amino group may be a primary (—$NH_2$), secondary (—NH-alkyl), or tertiary (—N(alkyl)$_2$) amino group, i.e. it may be substituted once or twice with an alkyl group as defined above.

In the context of this invention an alkylamino group is -alkyl-$NH_2$, alkyl-NH-alkyl or alkyl-N(alkyl)$_2$ wherein alkyl is as defined above.

In the context of this invention an alkylthio group is alkyl-SH, wherein alkyl is as defined above.

Examples of preferred aromatic heterocyclic monocyclic groups of the invention include 1,3,2,4- or 1,3,4,5-dioxadiazolyl, dioxatriazinyl, dioxazinyl, 1,2,3-, 1,2,4-, 1,3, 2- or 1,3,4-dioxazolyl, 1,3,2,4- or 1,3,4,5-dithiadiazolyl, dithiatriazinyl, dithiazinyl, 1,2,3-dithiazolyl, furanyl, furazanyl, imidazolyl, isoimidazolyl, 2-isoimidazolyl, isoindazolyl, isothiazolyl, isoxazolyl, 1,2,3-, 1,2,4-, 1,2,5- or 1,3,4-oxadiazolyl, oxatetrazinyl, oxatriazinyl, 1,2,3,4- or 1,2,3,5-oxatriazolyl, oxazolyl, pyrazinyl, pyrazolyl, pyridazinyl, pyridinyl, pyrimidinyl, pyrrolyl (azolyl), 1,2,3, 4- or 2,1,3,4-tetrazolyl, thiadiazolyl, thiazolyl, thienyl, 1,2, 3-, 1,2,4- or 1,3,5-triazinyl, and 1,2,3-, 1,2,4-, 2,1,3- or 4,1,2-triazolyl, furan-2-yl, furan-3-yl, 2-, 4- or 5-imidazolyl, 3-, 4- or 5-isoxazolyl, 1-, 2- or 3-pyridinyl, 1- or 2-thienyl.

In the context of this application, "label" stands for the binding of a marker to the compound of interest that will allow easy quantitative detection of said compound.

The labelled compound of the present invention preferably contains at least one radionuclide as a label. Positron emitting radionuclides are all candidates for usage. In the context of this invention the radionuclide is preferably selected from $^{11}C$, $^{18}F$, $^{15}O$, $^{13}N$, $^{123}I$, $^{125}I$, $^{131}I$, $^{3}H$ and $^{99m}Tc$.

The fluorescent group of the compound of formula (I) can be selected from the group of naturally occurring fluorophores or chemically synthesized fluorescent groups, such as rhodamine, green fluorescent protein or fluorescein and its derivatives.

It will be appreciated by those skilled in the art that some compounds of formula (I) contain chiral centres and that such compounds exist in the form of isomers (i.e. enantiomers). The invention includes all such isomers and any mixtures thereof including racemic mixtures.

Some of the compounds of formula (I) exist in (+) and (−) forms as well as in racemic forms. Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallisation of d- or I-(tartrates, mandelates, or camphorsulphonate) salts. The compounds of formula (I) may also be resolved by the formation of diastereomeric amides by reaction of the compounds of formula (I) with an optically active activated carboxylic acid such as that derived from (+) or (−) phenylalanine, (+) or (−) phenylglycine, (+) or (−) camphanic acid or by the formation of diastereomeric carbamates by reaction of the compounds of formula (I) e.g. with an optically active chloroformate.

Additional methods for the resolution of optical isomers, known to those skilled in the art may be used, and will be apparent to the average person skilled in the art. Such methods include those discussed by Jaques J, et al. [Jaques J. Collet A, and Wilen S; in *Enantiomers, Racemates, and Resolutions*, John Wiley and Sons, New York, 1981].

The labelled compounds of the invention may be prepared in numerous ways. The labelled compounds of the invention and their pharmaceutically acceptable derivatives may thus be prepared by any method known in the art for the preparation of compounds of analogous structure, provided that a label, preferably a radionuclide, is incorporated by suitable means.

The labelled compounds of the present invention can be prepared in the same way as the unlabelled compounds of formula (I) except that at least one of the materials used for the preparation of the compounds of formula (I) comprises a label, preferably a radionuclide, which label is inserted into the final compound. Alternatively, a group of an unlabelled compound of formula (I) can be exchanged by a labelled group, thereby forming a labelled compound of formula (I).

The unlabelled compounds of formula (I) can for example be prepared according to the methods disclosed in WO 97/13770, for example as in the following scheme (1).

Scheme (1)

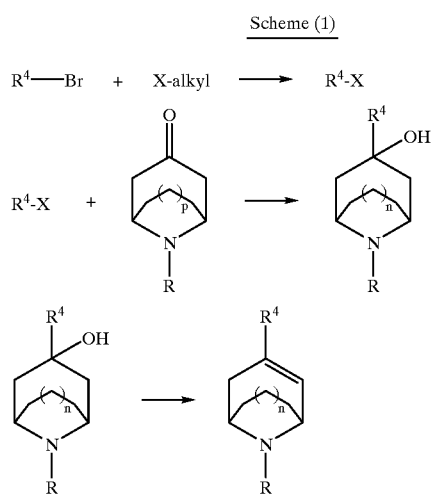

The non-ene derivatives are prepared by essentially analogous methods of preparation.

The substituents R and $R^4$ in the formulae of scheme (I) are as defined above and X is Li, MgBr or any other type of functional group suitable for generating a carbanion as its counterpart.

The processes in the reaction scheme above are carried out in conventional manner. The dehydration of the alcohol is affected using acids such as hydrochloric or sulphuric acid or other conventional dehydrating agents such as for example $P_2O_5$ or $SOCl_2$.

An unlabelled compound of formula (I) can be converted to another unlabelled compound of formula (I) using conventional methods.

The materials used in the preparation of unlabelled compounds of formula (I) are known or can be prepared by known processes from commercially available materials.

The products of the reactions described herein can be isolated by conventional means, such as extraction, crystallisation, distillation and/or chromatography.

The labelled compounds of formula (I) can generally be prepared in the same way as described above for the unlabelled compounds of formula (I). In this case, any of the materials used for the preparation of the unlabelled compound of formula (I) can be labelled, preferably by a radionuclide, in such a way that the label is incorporated into the finally prepared labelled compound of formula (I). Said labelled materials are either commercially available or can be prepared by using commercially available labelling agents.

An examples of commercially available labelling agents, which can be used in the preparation of the labelled compounds of the present invention is $[^{11}C]O_2$. $^{18}F$, NaI with different isotopes of iodine.

In particular $[C^{11}]O_2$ may be converted to a $[^{11}C]$-methylating agent, such as $[^{11}C]H_3I$ or $[^{11}C]$-methyl triflate. Labelled compounds containing e.g. $[^{125}I]$labelled 1-iodoprop-1-en-3-yl as substituent on N-8 may be prepared as described in the art [Elmaleh et. al.; *J. Nucl. Med.* 1996 37 1197–1202].

Labelled compounds containing e.g. $[^{18}F]$-alkyl substituted N-8 may be prepared as described in the art, e.g. in WO 96/39198.

Furthermore, labelled compounds of the present invention can, for example, be prepared by using labelled compounds $R^4X$ in the reaction shown in scheme (1) above, wherein $R^4$ and X are as defined above, except that $R^4$ contains a label. These compounds can be prepared by known methods. Illustrative examples of labelled compounds $R^4X$ are those, wherein $R^4$ is selected from $[^{11}C]H_3$-substituted phenyl, benzyl, heteroaryl and naphthyl groups, $[^{11}C]F_3$-substituted phenyl, benzyl, heteroaryl and naphthyl groups, $[^{11}C]N$-substituted phenyl, benzyl, heteroaryl and naphthyl groups, $H_3[^{11}C]O$-substituted phenyl, benzyl, heteroaryl and naphthyl groups, $[^{18}F]$-substituted phenyl, benzyl, heteroaryl and naphthyl groups, $[^{18}F]_3C$-substituted phenyl, benzyl, heteroaryl and naphthyl groups, $H_3C[^{15}O]$-substituted phenyl, benzyl, heteroaryl and naphthyl groups, a 3,4-methylenedioxyphenyl group containing at least one $[^{15}O]$, $N[^{15}O]_2$-substituted phenyl, benzyl, heteroaryl and naphthyl groups, $C[^{13}N]$-substituted phenyl, benzyl, heteroaryl and naphthyl groups, $[^{13}N]$amino-substituted phenyl, benzyl, heteroaryl and naphthyl groups, $[^{123}I]$, $[^{125}I]$ or $[^{131}I]$-substituted phenyl, benzyl, heteroaryl and naphthyl groups and substituted or unsubstituted phenyl, benzyl, heteroaryl and naphthyl groups containing at least one $[^{3}H]$ attached to the ring or contained in a substituted group.

As described above, an unlabelled compound of formula (I) can be converted to a labelled compound of formula (I) by using a labelling agent.

A labelled compound according to the present invention containing a $[^{11}C]H_3$-group can, for example, be prepared by reacting a free amine compound of formula (I), i.e. wherein R is H and $R^4$ is as defined above, with a $[^{11}C]$-methylating agent, preferably with $[^{11}C]H_3I$ or $[^{11}C]$-methyl triflate.

In analogy, other $[^{11}C]$ labelled groups R can be introduced, e.g. by reacting said free amine compound of formula (I) with a $[^{11}C]$ labelled alkylating agent optionally derivatised with a suitable leaving group (LG), such as $[^{11}C]$-cyclohexyl triflate or another suitable cycloalkyl alkylating agent. Other types of labelling of R of formula (I) includes e.g. alkyl substituted with $[^{125}I]$; alkenyl substituted with $[^{125}I]$; e.g. (1-$[^{125}I]$-prop-1-en-3-yl) as described in the art, (1-$[^{125}I]$-but-1-en-3-yl); and alkynyl substituted with $[^{125}I]$; or alkyl substituted with $[^{18}F]$, alkenyl substituted with $[^{18}F]$, alkynyl substituted with $[^{18}F]$; Standard leaving groups for use in these types of reaction are known in the art and some examples are mentioned below. Optionally the reaction may proceed through intermediate compounds such as the trialkyl tin derivatives, which is displaced by addition of Na[$^{125}$I] or [$^{18}$F].

In analogy, other labelled groups can be introduced to the R group e.g. by derivatising said free amine compound of formula (I), to contain a suitable leaving group which can be displaced by a labelled nucleofile. The leaving group being e.g. esters of sulphuric and sulfonic acids in general such as mesylate, tosylate, brosylate, nosylate, triflate, nonaflates, tresylates; Esters of nitrous acid, and inorganic ester leaving groups such as ROPO(OH)$_2$, ROB(OH)$_2$ halogen, conjugate acid of alcohol, ether, quarternary amines, tertiary sulphides, trialkyl tin derivatives etc., all known in the art; Performing the reaction in a suitable solvent, preferable polar, aprotic solvent and preferably essential free of water, with a labelled agent, acting as a nucleofile. Such nucleofile, as e.g. [$^{18}$F], may require auxiliary reagents to dissolve in the solvent. An auxiliary agent of the form M$^+$X$^-$, M$^+$ being i.e. 4,7,13,16,21,24-hexaoxa-1,10-diazabicyclo[8.8.8]hexacosane, alkali metal ions, tetraalkyammonium etc. as described in the art, and X$^-$ being e.g. carbonate, bicarbonate, hydroxide, formate or another counter ion, capable of dissolving radionuclides. Such compounds are known in the art.

As yet another embodiment of the invention, the compounds of formula(I) can represent substituents capable of coordinating to a metal complex. Such a metal could be isotopes of Tc whereby the complete complex formation is radiolabelled and suitable for diagnostic use [Meegall, S, et al.; *Bioconjugate Chem.* 1996 7 421–429]. Such substituents are e.g., alkylthio, alkenylthio, and alkynylthio.

The preparation of the labelled compounds according to the present invention is further illustrated by the working examples described below (Preparative Examples 1–4).

Pharmaceutical Compositions

The present invention further provides a pharmaceutical composition comprising a diagnostically effective amount of the labelled compound of formula (I) or mixtures thereof together with at least one pharmaceutically acceptable carrier or diluent, wherein the labelled compound of formula (I) is defined as disclosed above. The carrier or diluent must be "acceptable" in the sense of being compatible with the other ingredients of the formulation and not deleterious to the recipient thereof and is not specifically limited.

Pharmaceutical formulations include those suitable for parenteral administration, including intramuscular, subcutaneous and intravenous administration. Intravenous injection is the preferred way of administration.

Liquid form preparations include solutions, suspensions, and emulsions, for example, water or water-propylene glycol solutions. For example, parenteral injection liquid preparations can be formulated as solutions in aqueous polyethylene glycol solution.

The labelled compounds of the present invention may thus be formulated for parenteral administration (e.g. by injection) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the labelled compound of the present invention in water and adding suitable colorants, flavours, stabilising and thickening agents, as desired.

Aqueous suspensions suitable for oral use can be made by dispersing the finely divided labelled compound of the present invention in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. In addition to the labelled compound of the present invention, these preparations may, for example, contain colorants, flavours, stabilisers, buffers, artificial and natural sweeteners, dispersants, thickeners, and/or solubilizing agents.

Alternatively, the active ingredients may be provided in the form of a dry powder, for example a powder mix of the labelled compound of the present invention in a suitable powder base, such as lactose, starch, starch derivatives such as hydroxypropylmethyl cellulose and polyvinylpyrrolidone (PVP). The powder composition may be presented in unit dose form for example in capsules or cartridges of, e.g., gelatine, or blister packs.

Preferred compositions are tablets or capsules for oral administration and liquids for intravenous administration.

Suitable dosage ranges are in the range of from about 0.1 ng to about 100 μg of the labelled compounds of the present invention, administered in an appropriate dose, dependent as usual upon the exact mode and form of administration, the type of diagnosis, the subject involved and the body weight of the subject involved, and further the preference and experience of the physician or veterinarian in charge.

In further embodiments, the invention relates to

The use of a compound as above for the manufacture of a medicament for the treatment of a disorder or disease of a living animal body, including a human, which disorder or disease is responsive to the inhibition of monoamine neurotransmitter re-uptake in the central nervous system;

The use of a compound as above for the manufacture of a medicament for the treatment of a disorder or disease of a living animal body, including a human, which disorder or disease is responsive to the inhibition of serotonine re-uptake in the central nervous system;

The use of a compound as above for the manufacture of a medicament for the treatment of depression and related disorders such as pseudodementia or Ganser's syndrome, obsessive compulsive disorders, panic disorders, memory deficits, attention deficit hyperactivity disorder, obesity, anxiety and eating disorders; and The use as above wherein the compound employed is (±)-3-(4-trifluoromethoxyphenyl)-8-methyl-azabicyclo[3.2.1]oct-2-ene;

(±)-3-(4-trifluoromethoxyphenyl)-8-azabicyclo[3.2.1)oct-2-ene;

(±)-3-(4-cyanophenyl)-8-azabicyclo(3.2.1]oct-2-ene;

(±)-3-(4-cyanophenyl)-8-methyl-azabicyclo[3.2.1]oct-2-ene;

(±)-3-(4-nitrophenyl)-8-methyl-azabicyclo[3.2.1]oct-2-ene;

(±)-3-(4-nitrophenyl)-8-azabicyclo[3.2.1]oct-2-ene;

(±)-3-(4-(4,4,4,3,3,2,2,1,1-nona-fluoro-butyl-1-oxy)phenyl)-8-azabicyclo[3.2.1]oct-2-ene;

(±)-3-(4-(4,4,4,3,3,2,2,1,1-nona-fluoro-butyl-1-oxy)phenyl)-8-methyl-8-azabicyclo[3.2.1]oct-2-ene;

(±)-3-(4-(2,2,2-trifluoroethyl-1-oxy)phenyl)-8-azabicyclo[3.2.1]oct-2-ene;

(±)-3-(4-(2,2,2-trifluoroethyl-1-oxy)phenyl)-8-azabicyclo[3.2.1]oct-2-ene;

(±)-3-(4-(ethylen-1-oxy)phenyl)-8-azabicyclo(3.2.1]oct-2-ene;

(±)-3-(4-(ethylen-1-oxy)phenyl)-8-methyl-8-azabicyclo[3.2.1]oct-2-ene;

(±)-3-(4-(2-propylen-1-oxy)phenyl)-8-azabicyclo[3.2.1]oct-2-ene; or (±)-3-(4-(2-propylen-1-oxy)phenyl)-8-methyl-8-azabicyclo[3.2.1]oct-2-ene.

(±)3-[1-(4-trifluoromethoxyphenyl)]-9-azabicyclo[3.3.1]non-2-ene;

(±)3-[1-(4-trifluoromethylphenyl)]-9-azabicyclo[3.3.1]non-2-ene;

(±)-9-Methyl-3-[1-(4-trifluoromethoxyphenyl)]-9-azabicyclo[3.3.1]non-2-ene;

(±)-9-Methyl-3-[1-(4-trifluoromethylphenyl)]-9-azabicyclo[3.3.1]non-2-ene;

or a pharmaceutically acceptable addition salt thereof;

A method of treating a disorder or disease of a living animal body, including a human, which disorder or disease is responsive to the inhibition of monoamine neurotransmitter re-uptake, comprising the step of administering to such a living animal body, including a human, in need thereof a therapeutically effective amount of a compound as above;

A method of treating a disorder or disease of a living animal body, including a human, which disorder or disease is responsive to the inhibition of serotonine re-uptake, comprising the step of administering to such a living animal body, including a human, in need thereof a therapeutically effective amount of a compound as above;

The method as above wherein depression and related disorders such as pseudodementia or Ganser's syndrome, obsessive compulsive disorders, panic disorders, memory deficits, attention deficit hyperactivity disorder, obesity, anxiety or eating disorders are treated.

Biology

The compounds of the invention have been tested for their ability to inhibit reuptake of dopamine(DA) noradrenaline (NA) and serotonine(5-HT) in synaptosomes.

Background:

Specific neurotransmitter transporters/uptake sites on nerve terminals presumably function to terminate neuronal signalling by removing the neurotransmitters dopamine, noradrenaline and serotonine, respectively, from the synaptic cleft. The activity of the transporter integral proteins can be measured in vitro by synaptosomal uptake of $^3$H-dopamine, $^3$H-noradrenaline and $^3$H-serotonine, respectively.

In vitro Inhibition of $^3$H-dopamine ($^3$H-DA) Uptake in Striatal Synaptosomes Tissue preparations: Preparations are performed at 0–4° C. unless otherwise indicated. Corpi striati from male Wistar rats (150–200 g) are homogenised for 5–10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet (P$_2$) is resuspended in oxygenated (equilibrated with an atmosphere of 96% O$_2$: 4% CO$_2$ for at least 30 min) Krebs-Ringer incubation buffer (8000 ml per g of original tissue) at pH 7.2 containing 122 mM NaCl, 0.16 mM EDTA, 4.8 mM KCl, 12.7 mM Na$_2$HPO$_4$, 3.0 mM NaH$_2$PO$_4$, 1.2 mM MgSO$_4$, 1 mM CaCl$_2$, 10 mM glucose and 1 mM ascorbic acid.

Assay: Aliquots of 4.0 ml tissue suspension are added to 100 µl of test solution and 100 µl of $^3$H-DA (1 nM, final concentration), mixed and incubated for 25 min at 37° C. Non-specific uptake is determined using benztropine (10 µM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an IC$_{50}$.

The test value is given as IC$_{50}$ (the concentration (µM) of the test substance which inhibits the specific binding of $^3$H-DA by 50%).

In vitro Inhibition of $^3$H-noradrenaline ($^3$H-NA) Uptake in Hippocampal Synaptosomes Tissue preparation: Preparations are performed at 0–4° C. unless otherwise indicated. Hippocampi from male Wistar rats (150–200 g) are homogenised for 5–10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet (P$_2$) is resuspended in oxygenated (equilibrated with an atmosphere of 96% O$_2$: 4% CO$_2$ for at least 30 min) Krebs-Ringer incubation buffer (2000 ml per 9 of original tissue) at pH 7.2 containing 122 mM NaCl, 0.16 mM EDTA, 4.8 mM KCl, 12.7 mM Na$_2$HPO$_4$, 3.0 mM NaH$_2$PO$_4$, 1.2 mM MgSO$_4$, 0.97 mM CaCl$_2$, 10 mM glucose and 1 mM ascorbic acid.

Assay: Aliquots of 4.0 ml tissue suspension are added to 100 µl of test solution and 100 µl of $^3$H-NA (1 nM, final concentration), mixed and incubated for 90 min at 37° C. Non-specific uptake is determined using desipramine (1 µM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an IC$_{50}$.

The test value is given as IC$_{50}$ (the concentration (µM) of the test substance which inhibits the specific binding of $^3$H-NA by 50%).

In vitro Inhibition of $^3$H-5-hydroxytryptamine ($^3$H-5-HT, Serotonine) Uptake in Cortical Synaptosomes Tissue Preparation: Preparations are performed at 0–4° C. unless otherwise indicated. Cerebral cortices from male Wistar rats (150–200 g) are homogenised for 5–10 sec in 100 volumes of ice-cold 0.32M sucrose containing 1 mM pargyline using an Ultra-Turrax homogenizer. Monoamine oxidase activity will be inhibited in the presence of pargyline. The homogenate is centrifuged at 1000×g for 10 min. The resulting supernatant is then centrifuged at 27,000×g for 50 min and the supernatant is discarded. The pellet ($P_2$) is resuspended in oxygenated (equilibrated with an atmosphere of 96% $O_2$: 4% $CO_2$ for at least 30 min) Krebs-Ringer incubation buffer (1000 ml per g of original tissue) at pH 7.2 containing 122 mM NaCl, 0.16 mM EDTA, 4.8 mM KCl, 12.7 mM $Na_2HPO_4$, 3.0 mM $NaH_2PO_4$, 1.2 mM $MgSO_4$, 1 mM $CaCl_2$, 10 mM glucose and 1 mM ascorbic acid.

Assay: Aliquots of 4.0 ml tissue suspension are added to 100 µl of test solution and 100 µl of $^3$H-5-HT (1 nM, final concentration), mixed and incubated for 30 min at 37° C. Non-specific uptake is determined using citalopram (1 µM, final concentration). After incubation the samples are poured directly onto Whatman GF/C glass fibre filters under suction. The filters are then washed three times with 5 ml of ice-cold 0.9% (w/v) NaCl solution. The amount of radioactivity on the filters is determined by conventional liquid scintillation counting. Specific uptake is calculated as the difference between total uptake and non-specific uptake.

25–75% inhibition of specific binding must be obtained, before calculation of an $IC_{50}$.

The test value is given as $IC_{50}$ (the concentration (µM) of the test substance which inhibits the specific binding of $^3$H-5-HT by 50%).

Test results obtained by testing a selected compound of the present invention appear from the below tables.

TABLE 1

| Test compound | DA-uptake $IC_{50}$ (µM) | NA-uptake $IC_{50}$ (µM) | 5-HT-uptake $IC_{50}$ (µM) |
|---|---|---|---|
| (±)-3-(4-cyanophenyl)-8-methyl-8-azabicyclo(3.2.1)oct-2-ene | 18.00 | 4.90 | 0.047 |
| (±)-3-(4-nitrophenyl)-8-methyl-8-azabicyclo[3.2.1]oct-2-ene | 1.50 | 0.50 | 0.016 |
| (±)-3-(4-trifluoromethoxyphenyl)-8-methyl-8-azabicyclo[3.2.1]oct-2-ene | 22.00 | 8.00 | 0.0036 |

The results presented above show that the compounds are in vitro inhibitors of monoamine neurotransmitter re-uptake, in particular selective serotonine re-uptake inhibitors.

TABLE 2

| Test compound | DA-uptake $IC_{50}$ (µM) | NA-uptake $IC_{50}$ (µM) | 5-HT-uptake $IC_{50}$ (µM) |
|---|---|---|---|
| (±)-3-(4-trifluoromethoxy-phenyl)-8-methyl-8-aza-bicyclo[3.2.1]oct-2-ene (racemate) | 21.3 ± 1.2 | 12.0 ± 2.3 | 0.0035 ± 0.0003 |
| (±)-3-(4-trifluoro-methoxyphenyl)-8-aza-bicyclo[3.2.1]oct-2-ene (racemate) | 18.7 ± 3.5 | 15.6 ± 3.5 | 0.0048 ± 0.0006 |
| 3-(4-trifluoromethoxyphenyl)-8-azabicyclo[3.2.1]oct-2-ene (enantiomer A*) | | | 0.022 ± 0.012 |
| 3-(4-trifluoromethoxyphenyl)-8-azabicyclo[3.2.1]oct-2-ene (enantiomer B*) | | | 0.012 ± 0.006 |

*As the absolute stereochemical configuration of the enantiomers is presently unknown, they are arbitrarily named based on their order of elution from a DAICEL Chiralcel OD-H column; first off = A, second off = B.

The results shown in Table 2 obtained in vitro show that 3-(4-trifluoromethoxyphenyl)-8-methyl-8-azabicyclo[3.2.1] oct-2-ene (racemate) and 3-(4-trifluoromethoxyphenyl)-8-azabicyclo[3.2.1]oct-2-ene (racemate) are highly potent and selective serotonine re-uptake inhibitors. Both racemic compounds were significantly more potent as inhibitors of serotonine uptake than of either noradrenaline or dopamine uptake. It is noteworthy that the 3000-fold greater potency of the compounds as inhibitors of serotonine uptake than of either noradrenaline or dopamine uptake places them among the most selective serotonine re-uptake inhibitors currently known. There were no marked differences in vitro between the actions of the enantiomers of 3-(4-trifluoromethoxyphenyl)-8-azabicyclo[3.2.1]oct-2-ene and further studies also showed the same for the enantiomers of 3-(4-trifluoromethoxyphenyl)-8-methyl-8-azabicyclo[3.2.1] oct-2-ene.

The compounds of the invention have also been tested in the following test for antidepressant activity.

Diagnostic Methods and Method for in vivo Receptor Imaging (Neuroimaging)

The second object of the present invention is attained in a first embodiment of the invention by a method for determining the level of monoamine neurotransmitter re-uptake sites in a blood sample, said method comprising the steps of
(a) adding a compound of formula (I) or any of its enantiomers or a mixture thereof, or a pharmaceutically acceptable salt thereof in labelled or unlabelled form to a blood sample;
(b) measuring an amount of a compound of formula (I) bound to a predetermined part of the blood sample; and
(c) calculating the number of the monoamine neurotransmitter re-uptake sites in blood platelets from the data obtained in (b).

In the following, this method is also referred to as the "in-vitro method" of the present invention.

The in-vitro method especially allows to accurately calculate the serotonine re-uptake sites in a cellular fraction obtained in step (b). The predetermined part of the blood sample is preferably a blood fraction that contains the blood platelets.

In step (2) of the in-vitro method of the present invention a labelled or unlabelled compound of formula (I) or any of its enantiomers or a mixture thereof, or a pharmaceutically acceptable salt thereof is added to a blood sample. Generally, the compound of formula (I) added in step (a) is selected depending on the method of measuring the amount of the compound of formula (I) bound to said predetermined part of the blood sample used in step (b) of the in-vitro method of the invention.

In case a compound of formula (I) used in step (a) of the above mentioned method is a labelled compound of the present invention, this compound is preferably labelled with at least one radionuclide. Preferred radionuclides are those described above. In formula (I), R and $R^4$ are as defined above, and preferred groups R and $R^4$ are as defined above. Additionally, $R^4$ being a fluorescent group is preferred.

In step (a) of the in-vitro method of the present invention the compound of formula (I) may also be used in unlabelled form. In this case, R and $R^4$ are as defined above, and preferred groups R and $R^4$ are as defined above. Additionally, $R^4$ being a fluorescent group is preferred.

The labelled or unlabelled compound of formula (I) added in step (a) of the in vitro-method of the present invention can be detected by a suitable spectroscopic method, in particular UV spectroscopy and/or fluorescence spectroscopy.

In step (c) of the in-vitro method of the present invention, the level of the monoamine neurotransmitter re-uptake sites can be calculated from the data obtained in step (b) by using, for example, Scatchard Plot Analysis.

In a second embodiment, the second object of the present invention is solved by a method for the non-invasive determination of the distribution of a tracer compound inside a whole, intact living animal or human body using a physical detection method, wherein the tracer compound is a compound of formula (I) or any of its enantiomers and any mixture thereof, or a pharmaceutically acceptable salt thereof in its labelled or unlabelled form.

In the following, this method is also referred to as "in-vivo method" of the present invention.

The physical method for detecting said tracer compound of formula (I) in the in-vivo method of the present invention is preferably selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

The tracer compound of formula (I) can be selected in accordance with the detection method chosen. The compound of formula (I) as described above can be used in labelled form or in unlabelled form.

In case a labelled compound of formula (I) is used in the in-vivo method of the present invention, it is preferably labelled with a radionuclide, which is preferably selected from $^{11}C$, $^{18}F$, $^{15}O$, $^{13}N$, $^{123}I$, $^{125}I$, $^{131}I$ and $^{3}H$. Preferred examples of the labelled compound of formula (I) according to the present invention are given above.

The following table summarises preferred detection methods and the use of suitable radionuclides.

| Detection Method | Suitable Radionuclides |
| --- | --- |
| PET | $^{11}C$, $^{15}O$, $^{13}N$, $^{18}F$, $^{76}Br$, |
| SPECT | $^{123}I$, $^{125}I$, $^{131}I$ |

In case an unlabelled compound of formula (I) is used in the in-vivo method of the present invention, said compound preferably contains at least one $^{19}F$ containing substituent. Especially preferred unlabelled compounds of formula (I) are those, wherein $R^4$ is a phenyl group containing at least one substituent selected from $OCF_3$, $CN$ and $NO_2$.

Specific examples of unlabelled compounds of formula (I) which can be used in the in-vivo method of the present invention are (±)-3-(4-trifluoromethoxyphenyl)-8-methyl-azabicyclo [3.2.1]oct-2-ene;

(±)-3-(4-trifluoromethoxyphenyl)-8-azabicyclo[3.2.1]oct-2-ene;

(±)-3-(4-cyanophenyl)-8-azabicyclo[3.2.1]oct-2-ene;

(±)-3-(4-cyanophenyl)-8-methyl-azabicyclo[3.2.1]oct-2-ene;

(±)-3-(4-nitrophenyl)-8-methyl-azabicyclo[3.2.1]oct-2-ene;

(±)-3-(4-nitrophenyl)-8-azabicyclo[3.2.1]oct-2-ene;

(±)-3-(4-(4,4,4,3,3,2,2,1,1-nona-fluoro-butyl-1-oxy) phenyl)-8-azabicyclo[3.2.1]oct-2-ene;

(±)-3-(4-(4,4,4,3,3,2,2,1,1-nona-fluoro-butyl-1-oxy) phenyl)-8-methyl-8-azabicyclo[3.2.1]oct-2-ene;

(±)-3-(4-(2,2,2-trifluoroethyl-1-oxy)phenyl)-8-azabicyclo [3.2.1]oct-2-ene;

(±)-3-(4-(2,2,2-trifluoroethyl-1-oxy)phenyl)-8-azabicyclo [3.2.1]oct-2-ene;

(±)-3-(4-(ethylen-1-oxy)phenyl)-8-azabicyclo[3.2.1]oct-2-ene;

(±)-3-(4-(ethylen-1-oxy)phenyl)-8-methyl-8-azabicyclo [3.2.1]oct-2-ene;

(±)-3-(4-(2-propylen-1-oxy)phenyl)-8-azabicyclo[3.2.1]oct-2-ene; or (±)-3-(4-(2-propylen-1-oxy)phenyl)-8-methyl-8-azabicyclo [3.2.1]oct-2-ene.

(±)3-[1-(4-trifluoromethoxyphenyl)]-9-azabicyclo[3.3.1] non-2-ene;

(±)3-[1-(4-trifluoromethylphenyl)]-9-azabicyclo[3.3.1]non-2-ene;

(±)-9-Methyl-3-[1-(4-trifluoromethoxyphenyl)]-9-azabicyclo[3.3.1]non-2-ene;

(±)-9-Methyl-3-[1-(4-trifluoromethylphenyl)]-9-azabicyclo [3.3.1]non-2-ene;

or a pharmaceutically acceptable salt thereof.

Examples of physical detection methods which can be used for detecting unlabeled compounds of formula (I) are HPLC and Mass spectroscopy.

The compound of formula (I) or any of its enantiomers or any mixtures thereof in labelled or unlabelled form can be used as a diagnostic agent for the diagnosis of a disorder or disease of a living animal body, including a human, which disorder or disease is responsive to the inhibition of monoamine neurotransmitter re-uptake in the central nervous system. Especially preferred is the use of these compounds for the diagnosis of a disorder or disease which is responsive to the inhibition of serotonine neurotransmitter re-uptake. Furthermore, said labelled or unlabelled compound of formula (I) can be used for diagnosing a disorder or disease which is depression or a related disorder, such as pseudodementia or Ganser's syndrome, obsessive compulsive disorder, panic disorder, memory deficit, attention deficit hyperactivity disorder (ADHD syndrome), obesity, anxiety and eating disorder.

Before conducting the in-vivo method of the present invention, a diagnostically effective amount of a labelled or unlabeled compound of formula (I) is administered to a living body, including a human. Although the labelled or unlabelled compound of formula (I) can be administered as such, it is preferably administered in the form of a pharmaceutical composition.

In case a labelled compound of formula (I) is administered in the form of a pharmaceutical composition, the pharmaceutical composition of the present invention as described above can be used.

In case an unlabelled compound of formula (I) is administered in the form of a pharmaceutical composition, a pharmaceutical composition may be used, which differs from the above described pharmaceutical composition of the present invention in that it contains an unlabelled compound of formula (I) instead of the labelled compound of formula (I).

The diagnostically effective amount of the labelled or unlabelled compound of formula (I) to be administered before conducting the in-vivo method for the present invention is within a range of from 0.1 ng to 100 mg per kg body weight, preferably within a range of from 1 ng to 10 mg per kg body weight.

By using the in-vivo method of the present invention the distribution of said labelled or unlabelled compound of formula (I) can be determined by a physical method in the body or any desired part thereof. Preferably, the distribution in a part of the nervous system, especially preferred in the brain, is determined.

From the data obtained from the in-vivo method of the present invention, the extent of disease can be evaluated e.g. by a physician, preferably a neurologist. Said evaluation can especially be effected by comparing the data obtained from the in-vivo method of the present invention with control data. Said control data may, for example, be obtained from a control group of individuals. This group consists either of healthy individuals or of individuals who suffer from one of the above mentioned disorders or diseases.

Thus, the present invention further provides a method of diagnosis of a disorder or disease of a living human or animal body, which disorder or disease is responsive to the inhibition or monoamine neurotransmitter re-uptake, comprising the steps of (a) administering to said body a diagnostically effective amount of a compound of formula (I) in its labelled or unlabelled form, (b) detecting said compound and determining the distribution thereon in at least a part of said body by physical methods, and (c) comparing the obtained data with control data.

The pharmaceutical composition, which is preferably used in the in-vitro method of the present invention, can be provided in the form of an assay kit system wherein said pharmaceutical composition comprises either a labelled or unlabelled compound of formula (I) in unit-dosage form in a suitable container. Preferably, said unit dosage is adjusted to be sufficient for analysing one blood sample according to the in-vitro method of the invention. Furthermore, said assay kit of the present invention can further comprise a stabilising composition. The stabilising composition can be selected from antioxidants, such as Ascorbic Acid, or from buffers of weak acid-base composition e.g. phosphate buffers or from various types of cyclodextrins e.g. Hydroxypropyl β-Cyclodextrin.

The compounds and their derivatives of this invention are the first substances known that specifically bind to serotonine transporters. The compounds and their derivatives of this invention have a high selectivity for serotonine transporters and this applies specifically to the compounds given in the examples below, more specifically to compounds of formula (I), where $R^4$ is a phenyl group containing at least one substituent selected from $OCF_3$, CN and $NO_2$ and even more specifically to compounds of formula (I), where $R^4$ is a phenyl group substituted with at least one $OCF_3$ group.

This allows for the first time to reliably determine the number of serotonine binding sites and related Kd values and the release of serotonine as well as the detection of changes in the serotonine metabolism in response to therapeutic drugs.

Furthermore, a labelled compound of formula (I) may also be used in the analysis and adjustment of the treatment of patients having a lower level of serotonine re-uptake as compared to the normal level with serotonine uptake inhibitors. In this context, the compounds of the invention can be employed to assess whether the dosage of serotonine re-uptake inhibitors given is sufficient to occupy a high number of the serotonine transporter sites thereby blocking the re-uptake of serotonine and extending their presence and action within the synaptic cleft. The labelled compound of the invention can likewise be used to investigate whether an unnecessary high dose is given thereby blocking too many serotonine transporter sites and/or increasing the risk of unwanted side-effects. If a compound is given in a sufficient dose whereby maximal blocking of serotonine re-uptake is achieved, then higher doses will only increase the risk of side effects.

EXAMPLES

The invention is further illustrated with reference to the following examples which are not intended to be in any way limiting to the scope of the invention as claimed.

Example 1

Preparation Example

Preparation of Intermediate Compounds (±)-8-Methyl-3-trifluoromethanesulfonyl-oxy-8-azabicyclo[3.2.1]oct-2-ene To 8-methyl-8-azabicyclo[3.2.1]octan-3-one (12.65 g, 90.9 mmol) in tetrahydrofuran (300 ml), was added at −70° C.; sodium bis(trimethylsilyl)amide in tetrahydrofuran (77.5 ml, 77.5 mmol). The reaction mixture was stirred for 30 min at −70° C. N-phenylbis(trifluoromethane-sulfonamide) (32.5 g, 90.9 mmol) in tetrahydrofuran (200 ml) was added at −70° C. The reaction mixture was allowed to reach room temperature slowly and was stirred over night. Aqueous sodium hydroxide (0.1 M, 500 ml) was added and the mixture was extracted twice with ethyl acetate (200 ml). Chromatography on silica gel with dichloromethane and 10% ethanol as solvent gave the title compound as an oil. Yield 16.2 g, 45%.

Example 2

Preparation Example

Preparation of Unlabelled Compounds of Formula (I)

Method A (±)-8-Methyl-3-[1-(4-nitrophenyl)]-8-azabicyclo[3.2.1]oct-2-ene

A mixture of (±)-8-methyl-3-trifluoromethanesulfonyl-oxy-8-azabicyclo[3.2.1]oct-2-ene (3.0 g 12.2 mmol), hexamethylditin (5.0 g, 15.3 mmol), bis(triphenylphosphine) palladium (II)-dichloride (0.43 g, 0.61 mmol) and lithium chloride (1.55 g, 12.3 mmol) was stirred in 1.4-dioxane (25 ml, filtered through Al2O3) at 70° C. for 2 h. Then 4-Bromonitrobenzene (7.39 g, 36.6 mmol) was added followed by stirring at reflux overnight. Aqueous sodium hydroxide (100 ml, 1 M) was added followed by extraction three times with ethyl acetate (125 ml).

Chromatography on silica gel with dichloromethane, methanol and conc. ammonia (89:10:1) gave the title compound as an oil. Yield 1.64 g, 36%. The corresponding salt was obtained by addition of a diethyl ether and methanol mixture (9:1) saturated with fumaric acid. Yield 2.08 g. Mp 204–206° C.

(±)-3-[1-(4-Cyanophenyl)]-8-methyl-8-azabicyclo[3.2.1]oct-2-ene Fumaric Acid Salt Was prepared according to method A. Mp 161–162° C.

The following compounds can be prepared analogously:
(±)-3-(4-(4,4,4,3,3,2,2,1,1-nona-fluoro-butyl-1-oxy)phenyl)-8-methyl-8-azabicyclo[3.2.1]oct-2-ene;
(±)-3-(4-(2,2,2-trifluoroethyl-1-oxy)phenyl)-8-methyl-8-azabicyclo[3.2.1]oct-2-ene;
(±)-3-(4-(ethylen-1-oxy)phenyl)-8-methyl-8-azabicyclo[3.2.1]oct-2-ene;
(±)-3-(4-(2-propylen-1-oxy)phenyl)-8-methyl-8-azabicyclo[3.2.1]oct-2-ene;

Method B (±)-8-Methyl-3-[1-(4-trifluoromethoxyphenyl)]-8-azabicyclo[3.2.1]oct-2-ene To a mixture of 1-bromo-4-trifluoromethoxybenzene (15.0 g, 62.2 mmol) and diethyl ether (200 ml), butyllithium in hexanes (28 ml, 68.5 mmol) was added at −70° C. The mixture was stirred at −70° C. for 1 h. 8-Methyl-8-azabicyclo[3.2.1]octan-3-one (8.7 g, 62.5 mmol) solved in diethyl ether (50 ml) was added at −70° C. and stirred for 1 h. The reaction mixture was allowed to warm to room temperature overnight. Aqueous sodium hydroxide (1 M, 100 ml) was added and crystals precipitated. The crystals were filtered. Endo and exo-3-hydroxy-8-methyl-3-[1-(4-trifluoromethoxy-phenyl]-8-azabicyclo[3.2.1]octane was isolated after trituration with petroleum ether (100 ml). Yield 12.5 g, 67%. To a mixture of endo and exo-3-hydroxy-8-methyl-3-[1-(4-trifluoromethoxyphenyl]-8-azabicyclo[3.2.1]octane (6.3 g, 20.9 mmol): was added hydrochloric acid (100 ml, 25%). The mixture was stirred at reflux for 30 min. The hydrochloric acid was evaporated. Sodium hydroxide (50 ml, 4 M) was added, followed by extraction with diethyl ether. (±)-8-Methyl-3-[1-(4-trifluoromethoxyphenyl)]-8-azabicyclo[3.2.1]oct-2-ene was isolated as an oil. Yield 4.1 g, 70%.

(±)-9-Methyl-3-[1-(4-trifluoromethoxyphenyl)]-9-azabicyclo[3.3.1]non-2-ene fumaric acid salt was prepared according to method B. Mp 159.2–160.7° C.

(±)-9-Methyl-3-[1-(4-trifluoromethylphenyl)]-9-azabicyclo[3.3.1]non-2-ene fumaric acid salt Was prepared according to method B. Mp 145.6–148.1° C.

Example 3

Preparation Example

Preparation of Unlabelled Compounds of Formula (I)

(±)-3-(4-Chlorophenyl)-8-azabicyclo[3.2.1]oct-2-ene Malonate

To a stirred solution of 3-(4-chlorophenyl)-8-methyl-8-azabicyclo[3.2.1]oct-2-ene (2 g, 8.5 mmol) in anhydrous 1,2-dichloroethane (20 ml) under nitrogen atmosphere 1-chloroethyl chloroformate (1.25 ml, 11.6 mmol) was added. The reaction mixture was heated at reflux overnight, then 1-chloroethyl chloroformate (1 ml, 9.3 mmol) was added and once again the reaction mixture was heated at reflux overnight. The reaction mixture was concentrated to an oil and the oil was dissolved in methanol (25 ml). This solution was heated at reflux for 2 hours and then concentrated to an oil. The residue was dissolved in water and concentrated $NH_4OH$ was added until pH 10 was reached. The water phase was extracted with diethyl ether. The organic phase was dried with magnesium sulphate and concentrated to dryness. The residue was chromatographed over silica gel (dichloromethane/ace-tone/methanol, 4/1/1 (v/v)). The product fractions were concentrated to an oil, the oil was dissolved in ethanol (96%) and malonic acid (0.55 g, 5.3 mmol) in ethanol (96%) was added. This solution was concentrated to an oil, the oil was triturated in diethyl ether. The title compound precipitated as a powder and was isolated by filtration. Yield (1.32 g, 48%), m.p. 136.1–138° C.

The following compound was prepared analogously:
(±)3-[1-(4-nitrophenyl)]-8-azabicyclo[3.2.1]oct-2-ene;
(±)3-[1-(4-cyanophenyl)]-8-azabicyclo[3.2.1]oct-2-ene;
(±)3-[1-(4-trifluoromethoxyphenyl)]-8-azabicyclo[3.2.1]oct-2-ene fumaric acid salt, mp 195–200° C.;
(±)3-[1-(4-trifluoromethoxyphenyl)]-8-azabicyclo [3.2.1]oct-2-ene, di-fumaric acid salt; m.p. 195–200° C.;
(±)-3-(4-(4,4,4,3,3,2,2,1,1-nona-fluoro-butyl-1-oxy)phenyl)-8-azabicyclo[3.2.1]oct-2-ene;
(±)-3-(4-(2,2,2-trifluoroethyl-1-oxy)phenyl)-8-azabicyclo-[3.2.1]oct-2-ene;
(±)-3-(4(ethylen-1-oxy)phenyl)-8-azabicyclo[3.2.1]oct-2-ene;
(±)-3-(4-(2-propylen-1-oxy)phenyl)-8-azabicyclo[3.2.1]oct-2-ene.
(±)3-[1-(4-trifluoromethoxyphenyl)]-9-azabicyclo[3.3.1]non-2-ene fumaric acid salt, mp 216–219° C.;
(±)3-[1-(4-trifluoromethylphenyl)]-9-azabicyclo[3.3.1]non-2-ene fumaric acid salt, mp 206–208° C.

Example 4

Preparation Example

Preparation of Labelled Compounds of Formula (I)

Preparation of [$^{11}$C]Methyl Iodide

[$^{11}$C]Carbon dioxide was prepared by the 14N(p,a)$^{11}$C nuclear reaction using a nitrogen gas target and 16 MeV protons produced by a GE Medical Systems PETtrace cyclotron.

[$^{11}$C]Carbon dioxide was purged from the target in a stream of nitrogen gas and trapped on 4 Å molecular sieves. On heating, the [$^{11}$C]$O_2$ was released and passed through a solution of $LiAlH_4$ in anhydrous tetrahydrofuran (THF; 300 ml). On completion of [$^{11}$C]$O_2$ transfer, the THF was evaporated and 1 ml hydroiodic acid was added. On heating at 160° C. the [$^{11}$C]methyl iodide formed was distilled in a stream of nitrogen gas to a reaction vial containing the labelling precursor.

Synthesis and Purification of [$^{11}$C] Labelled (±)8-methyl-3-(4-trifluoromethylphenyl)-8-azabicyclo [3.2.1]oct-2-ene (Compound 3-4)

(±)-3-(4-trifluoromethylphenyl)-8-azabicyclo[3.2.1]oct-2-ene in the form of a free amine (1 mg) was dissolved in anhydrous dimethyl sulphoxide (DMSO; 300 ml), and then reacted with [$^{11}$C]-methyl iodide and heated for 5 min at 130° C. The resulting N-[$^{11}$C]-methyl labelled [$^{11}$C]-compound was subsequently purified by HPLC. Removal of the HPLC solvent was achieved by heating the [$^{11}$C]-labelled (±)8-methyl-3-(4-trifluoromethylphenyl)-8-azabicyclo[3.2.1]oct-2-ene containing fraction under reduced pressure. The labelled product was then formulated in saline or water (10 ml) and passed over a 0.22 mm membrane filter into a sterile vial.

Synthesis and Purification of [$^{11}$C] Labelled (±)-(3, 4-dichlorophenyl)-8-methyl-8-azabicyclo [3.2.1]oct-2-ene (±)-3-(3,4-dichlorophenyl)-8-azabicyclo[3.2.1]oct-2-ene malonate was dissolved in DMSO (300 ml) and 0.5 mg NaOH were added thereto. The resulting mixture was then reacted with [$^{11}$C]-methyliodide under heating for 5 min at 130° C. The purification was conducted in analogy to the purification of the compound above.

The following compounds can be prepared and purified analogously.
[$^{11}$C] labelled 3-[1-(4-nitrophenyl)]-8-methyl-8-azabicyclo[3.2.1]oct-2-ene;
[$^{11}$C] labelled 3-[1-(4-cyanophenyl)]-8-methyl-8-azabicyclo[3.2.1]oct-2-ene;
[$^{11}$C] labelled 3-[1-(4-trifluoromethoxyphenyl)]-8-methyl-8-azabicyclo[3.2.1]oct-2-ene;
[$^{11}$C] labelled (±)-3-(4-(4,4,4,3,3,2,2,1,1-nona-fluoro-butyl-1-oxy)phenyl)-8-methyl-8-azabicyclo[3.2.1]oct-2-ene;

[$^{11}$C] labelled (±)-3-(4(2,2,2-trifluoroethyl-1-oxy)phenyl)-8-methyl-8-azabicyclo[3.2.1]oct-2-ene;
[$^{11}$C] labelled (±)-3-(4-(ethylen-1-oxy)phenyl)-8-methyl-8-azabicyclo[3.2.1]oct-2-ene;
[$^{11}$C] labelled (±)-3-(4-(2-propylen-1-oxy)phenyl)-8-methyl-8-azabicyclo[3.2.1]oct-2-ene;
[$^{11}$C] labelled (±)3-[1-(4-trifluoromethoxyphenyl)]9-azabicyclo[3.3.1]non-2-ene;
[$^{11}$C] labelled (±)3-[1-(4-trifluoromethylphenyl)]-9-azabicyclo[3.3.1]non-2-ene;
[$^{11}$C] labelled (±)-9-Methyl-3-[1-(4-trifluoromethoxyphenyl)]-9-azabicyclo[3.3.1]non-2-ene;
[$^{11}$C] labelled (±)-9-Methyl-3-[1-(4-trifluoromethylphenyl)]-9-azabicyclo[3.3.1]non-2-ene;

The labelled products were synthesised in less than 30 minutes. The following characteristics were determined for Compounds 1-4, 2-4, 3-4 and 4-4:
Radiochemical purity: >98%.
Typical mass of compounds in the final product: 30–60 nmol in a 10 ml formulation.
Typical radioactivity of final product: 1–4 GBq.
Typical specific activity: 30–100 GBq/mmol.

Example 5

In vivo Administration of [$^{11}$C] labelled (±)-3-(4-trifluoromethylphenyl)-8-methyl-8-azabicyclo[3.2.1]oct-2-ene The compound was used as a marker for the number of serotonine transporter sites. The binding of labelled compound to the serotonine transporter sites was measured as follows.
Experimental Animals
As test animals three female pigs (Hampshire x Yorkshire x Duroc x Landrace crossbred) weighing 39 to 44 kg were used. They were housed singularly in a thermostatically controlled (20° C.) animal colony with natural lighting conditions. The pigs had free access to water but were deprived of food for 24 hours prior to experiments.
Pigs were sedated with an i.m. injection of Midazolam (0.5 mg/kg) and Ketamine HCl (10 mg/kg). After 10 to 15 minutes a catheter was installed in an ear vein through which a mixture of Midazolam (0.25 mg/kg) and Ketamine (5 mg/kg) was administered. The pigs were then incubated and anaesthetised with Isoflourane in $O_2/N_2O$. Catheters (Avanti® size 4F–7F) were surgically installed in a femoral artery and vein. Infusions of isotonic saline (ca. 100 $cm^5$/h) and 5% of glucose (ca. 20 $cm^3$/h) were administered i.v. throughout the experiments. Body temperature was thermostatically maintained in the normal range (39.0–39.4° C.) and physiological functions (i.e. blood pressure, heart rate and expired air $CO_2$) were monitored continuously. Hematocrit and whole blood acid-base parameters (i.e. pH, $pCO_2$, $pO_2$, $HCO_3$ and $O_2$ saturation) were measured and disturbances in body fluid balance were corrected by appropriate procedures (e.g. force ventilation and/or changes in infusion rates).
PET Neuroimaging
The pigs were studied in the supine position in the scanner (Siemens ECAT EXACT HR) using a custom-made head-holding device. The regional distribution and binding of Compound (3-4) in pig brain was studied by administering an i.v. dose of ca. 10 mg followed immediately by an i.v. injection of heparin solution to flush the catheter. Scanning began on injection of Compound (3-4) and consisted of 28 frames (6×10 seconds, 4×30 seconds, 7×1 minute, 5×2 minutes, and 5×10 minutes). Under control conditions, no further injections were given during the scanning period. Under conditions of antidepressant treatment, an intravenous dose of 5 mg/kg was administered at 20 minutes after injection of the compound in order to determine whether the antidepressant drug influenced the cerebral binding, kinetics and distribution of the tracer compound.
Blood Sampling
A sequence of twenty-eight arterial blood samples (1–2 ml) were drawn from the pigs for determination of total plasma radioactivity concentration of Compound (3-4) at the following times: 18×10 seconds, 4×30 seconds, 5×1 minute, 7×5 minutes, and 1×15 minutes). Total plasma radioactivity was measured and metabolite correction was carried out using 200 µl plasma from the samples drawn at 0.5, 2, 10, 30 and 60 minutes (200 µl plasma alkalinised with 10 µl 50% NaOH and to which 400 ml ethyl acetate was added).
200 ml of the organic layer was removed and the quantity of $^{11}$C radioactivity was determined. Plasma levels of un-metabolised Compound (3-4) per $cm^3$ plasma were obtained by decay correcting the $^{11}$C count to start of scanning and multiplying by the dilution factor. Arterial samples obtained after infusion of Citalopram were used for HPLC estimation of the concentration of Citalopram in plasma.
Metabolite Analysis
Acetonitrile (0.05 ml) was added to plasma samples for metabolite analysis. After centrifugation, supernatant was loaded into a 1 ml injection loop and chromatographed using the analytical HPLC conditions stated above. The amount of uncharged Compound (3-4) was determined by integration of the radiopeak corresponding to Compound (3-4) in relation to the sum of all radioanalytes. Biexponential fitting of the data to the total plasma radioactivity concentration was performed to generate a metabolie-corrected input function. The rate of metabolism of Compound (3-4) was determined by multilinear curve-fitting based on the appearance of plasma metabolites from the metabolite-corrected plasma time-activity curve.
Pharmacokinetic Analysis
Seven brain regions of interest (ROIs) were identified using a neuroanatomical atlas of the pig brain [Yoshikawa, T; *Atlas of the brains of domestic animals*; Pennsylvania State University Press, University Park, Penn., 1968]. For each region, radioactivity concentrations were calculated for the sequence of frames, were corrected for the radioactive decay of $^{11}$C (20.3 min), and were plotted versus time. The data for illustrations were expressed in terms of standard uptake values (SUV), i.e. [radioactivity in ROI (Bq/cc) X body weight (g)/injected dose of radioactivity (Bq)]. Normalisation of the data was carried out by dividing SUVs obtained at a particular time in the ROI by SUVs in the cerebellum, a region devoid of neuronal serotonine transporters. The cerebellum (CB) was also used as reference region for determination of binding potential. Binding potential (B.P.) was calculated as follows:

$$B.P.=B_{ROI}/F=[A_{ROI}-A_{CB}/A_{CB}]-1]=\{[(K_{1\ ROI}/k_{2'ROI})/(K_{1\ CB}/k_{2CB})]-1\}.$$

Estimations of pharmacokinetic parameters for a two-component model was carried out using custom-made software based on the word of Gjedde and Wong [Gjedde, A.; Wong, D. F.: Modelling neuroreceptor binding of radioligands in vivo. Quantitative imaging; in *Neuroreceptors, Neurotransmitters, and Enzymes* (Frost. J. J. and Wagner, Jr.

H. N. (Eds.), Raven Press, New York. 1991 51–79], $K_1$ expresses the unidirectional clearance of the tracer from the circulation to the single tissue compartment, $k_2$ in the case of the cerebellum is the true rate constant for clearance from the brain, whereas $k_2'$ is an apparent rate constant of clearance from the single tissue compartment, assuming that equilibration between tissue compartments of solution and of binding are so rapid that a single compartment results. The $K_1/k_2'$ ratio is termed the apparent partition volume and expresses the binding of the compound in the ROI.

Example 6

In vitro Diagnosis

Reuptake of Serotonine into Platelets

Platelet-rich plasma was obtained by centrifugation of blood samples at 200×g for 10 min at 20° C. Platelet membranes were prepared by lysis and homogenisation of the platelet pellet following the method of Plenge and Mellerup [Plenge P & Mellerup ET: [³H]Citalopram binding to brain and platelet membranes of human and rat; *J. Neurochem.* 1991 56 248–252].

Aliquots of 500 µl membrane suspension were added to 25 µl of [³H]-X, mixed and incubated for 60 min at 2° C. Non-specific binding was determined using Paroxetine (1 µM, final concentration). After incubation the samples were added 5 ml of ice-cold buffer and poured directly onto Whatman GF/C fibre filters under suction and immediately washed with 5 ml ice-cold buffer.

The amount of radioactivity on the filters were determined by conventional liquid scintillation counting. Five to six concentrations of [³H]-X were used in the incubation mixture to determine the density of binding sites (Bmax) by Scatchard analysis.

In an Eppendorf tube containing 25 µl [¹⁴C]-5HT was added 375 ml PRP (platelet rich plasma) and incubated at 37° C. for 12(±)1 min. Each sample was incubated in triplicate. Incubations were terminated by the addition of 400 µl ice cold stopping solution (40 mM EDTA in 100 mM NaCl) and an aliquot of 200 µl was removed and placed in a scintillation vial ready to be counted for radioactivity. The remaining incubation mixture was rapidly centrifuged at >1500×g for 2 min. After centrifugation a 200 µl aliquot of the supernatant was removed and added to scintillation vials. 10 ml scintillation fluid was added to each vial and counted for 5 min in a liquid scintillation counter. Triplicate determinations were made for each sample. The percentage uptake of [¹⁴C]-5HT for each sample was calculated from the mean of the triplicate counts.

What is claimed is:

1. A chemical compound represented by the general formula

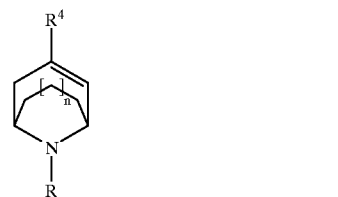

(I)

wherein
n is 0 or 1;
R is hydrogen alkyl, haloalkyl, alkenyl, haloalkenyl alkynyl, haloalkynyl, cycloalkyl, cycloalkyalkyl, or 2-hydroxyethyl, alkylamino, alkenylthio, alkynylthio or a leaving group; and
$R^4$ is phenyl substituted one or more times with —O—R", wherein (R") represents haloalkyl,
or any enantiomer of a compound of formula (I), or any mixture thereof, or any radioactively labelled compound of formula (I) or a pharmaceutically acceptable salt thereof.

2. The chemical compound of claim 1, wherein R is hydrogen alkyl, haloalkyl, alkylamino, alkythio, or a leaving group.

3. The chemical compound of claim 1, wherein R is hydrogen, alkyl, haloalkyl, haloalkenyl, alkylthio or a leaving group.

4. The chemical compound of any of the claims 1–3, said compound being:
(±)-3-(4-trifluoromethoxyphenyl)-8-methyl-azabicyclo[3.2.1]oct-2-ene;
(±)-3-(4-trifluoromethoxyphenyl)-8-azabicyclo[3.2.1]oct-2-ene;
(±)-3-(4-(4,4,4,3,3,2,2,1,1-nona-fluoro-butyl-1-oxy)phenyl)-8-azabicyclo[3.2.1]oct-2-ene;
(±)-3-(4-(4,4,4,3,3,2,2,1,1-nona-fluoro-butyl-1-oxy)phenyl)-8-methyl-8-azabicyclo[3.2.1]oct-2-ene;
±)-3-(4-(2,2,2-trifluoroethyl-1-oxy)phenyl)-8-azabicyclo[3.2.1]oct-2-ene;
(±)-3-(4-(2,2,2-trifluoroethyl-1-oxy)phenyl)-8-azabicyclo[3.2.1]oct-2-ene;
(±)3-[1-(4-trifluoromethoxyphenyl)]-9-azabicyclo[3.3.1]non-2-ene;
(±)-9-Methyl-3-[1-(4-trifluoromethoxyphenyl)]-9-azabicyclo[3.3.1]non-2-ene;
or a pharmaceutically acceptable addition salt thereof.

5. A pharmaceutical composition, comprising a therapeutically effective amount of a chemical compound of claim 1, together with at least one pharmaceutically acceptable carrier or diluent.

* * * * *

UNITED STATES PATENT AND TRADEMARK OFFICE
CERTIFICATE OF CORRECTION

PATENT NO. : 6,617,459 B2
DATED : September 9, 2003
INVENTOR(S) : Peters et al.

It is certified that error appears in the above-identified patent and that said Letters Patent is hereby corrected as shown below:

Title page,
Item [*] Notice: should read as follows:
-- Subject to any disclaimer, the term of this patent is extended or adjusted under 35 U.S.C. 154(b) by 15 days --

Signed and Sealed this

Sixth Day of April, 2004

JON W. DUDAS
*Acting Director of the United States Patent and Trademark Office*